US012217410B2

(12) United States Patent
Gorsky et al.

(10) Patent No.: US 12,217,410 B2
(45) Date of Patent: Feb. 4, 2025

(54) DECAY DETECTION SYSTEM

(71) Applicant: SUNKIST GROWERS, INC., Valencia, CA (US)

(72) Inventors: Aaron Gorsky, Valencia, CA (US); Tim Conway, Valencia, CA (US)

(73) Assignee: SUNKIST GROWERS, INC., Valencia, CA (US)

(*) Notice: Subject to any disclaimer, the term of this patent is extended or adjusted under 35 U.S.C. 154(b) by 502 days.

(21) Appl. No.: 17/606,497

(22) PCT Filed: May 8, 2020

(86) PCT No.: PCT/US2020/032036
§ 371 (c)(1),
(2) Date: Oct. 26, 2021

(87) PCT Pub. No.: WO2020/231784
PCT Pub. Date: Nov. 19, 2020

(65) Prior Publication Data

US 2022/0207709 A1 Jun. 30, 2022

Related U.S. Application Data

(60) Provisional application No. 62/846,040, filed on May 10, 2019.

(51) Int. Cl.
*G06T 7/00* (2017.01)
*G01N 21/33* (2006.01)
(Continued)

(52) U.S. Cl.
CPC .......... *G06T 7/0004* (2013.01); *G01N 21/33* (2013.01); *G01N 21/4738* (2013.01);
(Continued)

(58) Field of Classification Search
CPC .................... G06T 7/0004; G06T 7/70; G06T 2207/10064; G06T 2207/30128;
(Continued)

(56) References Cited

U.S. PATENT DOCUMENTS 5,845,002 A 12/1998 Heck et al.
7,860,277 B2 12/2010 Mulder et al.
(Continued)

FOREIGN PATENT DOCUMENTS

JP 5875186 B2 3/2016
JP 2018-59775 A 4/2018
(Continued)

OTHER PUBLICATIONS

D. Lorente et al., Early decay detection in citrus fruit using laser-light backscattering imaging. Apr. 12, 2013, Postharvest biology and technology, pp. 424-430. (Year: 2013).*
(Continued)

*Primary Examiner* — Diane D Mizrahi
(74) *Attorney, Agent, or Firm* — Sughrue Mion, PLLC

(57) ABSTRACT

A method may include obtaining a laser image of a food product. The method may include obtaining an ultraviolet (UV) image of the food product. The method may include determining a decay value of the food product, based on obtaining the laser image of the product and obtaining the UV image of the food product.

19 Claims, 16 Drawing Sheets

(51) Int. Cl.

| | |
|---|---|
| ***G01N 21/47*** | (2006.01) |
| ***G01N 21/64*** | (2006.01) |
| ***G01N 21/84*** | (2006.01) |
| ***G01N 21/85*** | (2006.01) |
| ***G01N 21/88*** | (2006.01) |
| ***G01N 33/02*** | (2006.01) |
| ***G06T 7/70*** | (2017.01) |

(52) U.S. Cl.
CPC ......... *G01N 21/6486* (2013.01); *G01N 21/85* (2013.01); *G01N 21/8851* (2013.01); *G01N 33/025* (2013.01); *G06T 7/70* (2017.01); *G01N 2021/845* (2013.01); *G06T 2207/10064* (2013.01); *G06T 2207/30128* (2013.01)

(58) Field of Classification Search
CPC .... G01N 21/33; G01N 21/6486; G01N 21/85; G01N 21/8851; G01N 2021/845
See application file for complete search history.

(56) References Cited

U.S. PATENT DOCUMENTS

| | | | |
|---|---|---|---|
| 8,159,525 | B2 | 4/2012 | Park et al. |
| 9,042,967 | B2 | 5/2015 | Dacosta et al. |
| 2005/0122524 | A1 | 6/2005 | Ibarra et al. |
| 2009/0185182 | A1 | 7/2009 | Kim et al. |
| 2018/0114597 | A1 | 4/2018 | Grabiner et al. |

FOREIGN PATENT DOCUMENTS

| | | | |
|---|---|---|---|
| WO | 2013/096243 | A1 | 6/2013 |
| WO | 2018/044327 | A1 | 3/2018 |

OTHER PUBLICATIONS

Extended European Search Report dated May 10, 2023 in European Application No. 20805534.3.
Lorente D et al., "Early decay detection in citrus fruit using laser-light backscattering imaging", Postharvest Biology and Technology, 2013, vol. 86, pp. 424-430 (7 pages total).
International Search Report of PCT/US2020/032036 dated Jul. 29, 2020 [PCT/ISA/210].
Written Opinion of PCT/US2020/032036 dated Jul. 29, 2020 [PCT/ISA/237].

* cited by examiner

DECAY DETECTION SYSTEM

CROSS-REFERENCE TO RELATED APPLICATION(S)

This application is a National Stage of International Application No. PCT/US2020/032036, filed May 8, 2020, claiming priority under 35 U.S.C. § 119 to U.S. Provisional Patent Application No. 62/846,040, filed on May 10, 2019, in the U.S. Patent & Trademark Office, the disclosure of which is incorporated by reference herein in its entirety.

BACKGROUND

After being harvested, citrus fruit (e.g., oranges, lemons, limes, etc.) is typically processed in a packing facility before being shipped to a particular destination. During processing, a worker may visually inspect the citrus fruit for visible defects, and remove particular citrus fruit exhibiting such defects. In this way, citrus fruit that is unsuitable for sale or consumption may be removed during the processing stage.

Various factors cause decay in the citrus fruit. During the onset of decay, the citrus fruit may undergo latent changes in appearance, and, as such, the decay may be relatively unnoticeable to a worker or an optical imaging system. As such, a worker or optical imaging system may fail to detect and remove citrus fruit having latent decay during the processing stage. In this case, the citrus fruit may contaminate other citrus fruit, thereby reducing yield.

SUMMARY

According to an aspect of an example embodiment, a method may include obtaining a laser image of a food product; obtaining an ultraviolet (UV) image of the food product; and determining a decay value of the food product, based on obtaining the laser image of the product and obtaining the UV image of the food product.

According to an aspect of an example embodiment, a device may include a memory configured to store instructions; and a processor configured to execute the instructions to: obtain a laser image of a food product; obtain an ultraviolet (UV) image of the food product; and determine a decay value of the food product, based on obtaining the laser image of the product and obtaining the UV image of the food product.

According to an aspect of an example embodiment, a non-transitory computer-readable medium may store instructions that, when executed by one or more processors of a device, cause the one or more processors to: obtain a laser image of a food product; obtain an ultraviolet (UV) image of the food product; and determine a decay value of the food product, based on obtaining the laser image of the product and obtaining the UV image of the food product.

DETAILED DESCRIPTION

Figure 1:
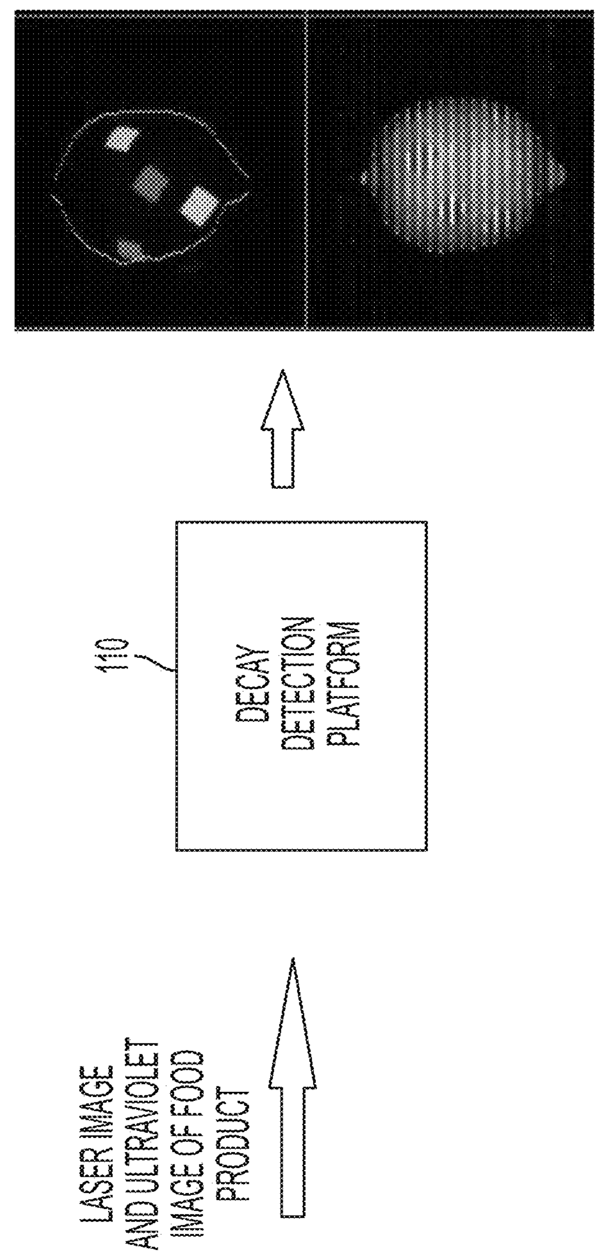
FIG. 1 is a diagram of an overview of an implementation according to an embodiment.

FIG. 1 is a diagram of an overview of an implementation according to an embodiment. An imaging system may capture a laser image and a UV image of a food product as the food product passes the imaging system on a conveyor in a food processing facility. The imaging system may provide the laser image and the UV image of the food product to the decay detection platform. The decay detection platform may determine a decay value of the food product based on the laser image and/or the UV image, and perform an action based on the decay value. For example, the decay detection platform may cause the food product to be removed from the conveyor. In this way, the decay detection platform may detect food products that are afflicted with early decay and/or late decay, and/or that exhibit latent manifestations of decay. Further, in this way, the embodiments herein improve yield by reducing the likelihood of such food products from causing contamination.

Figure 2:
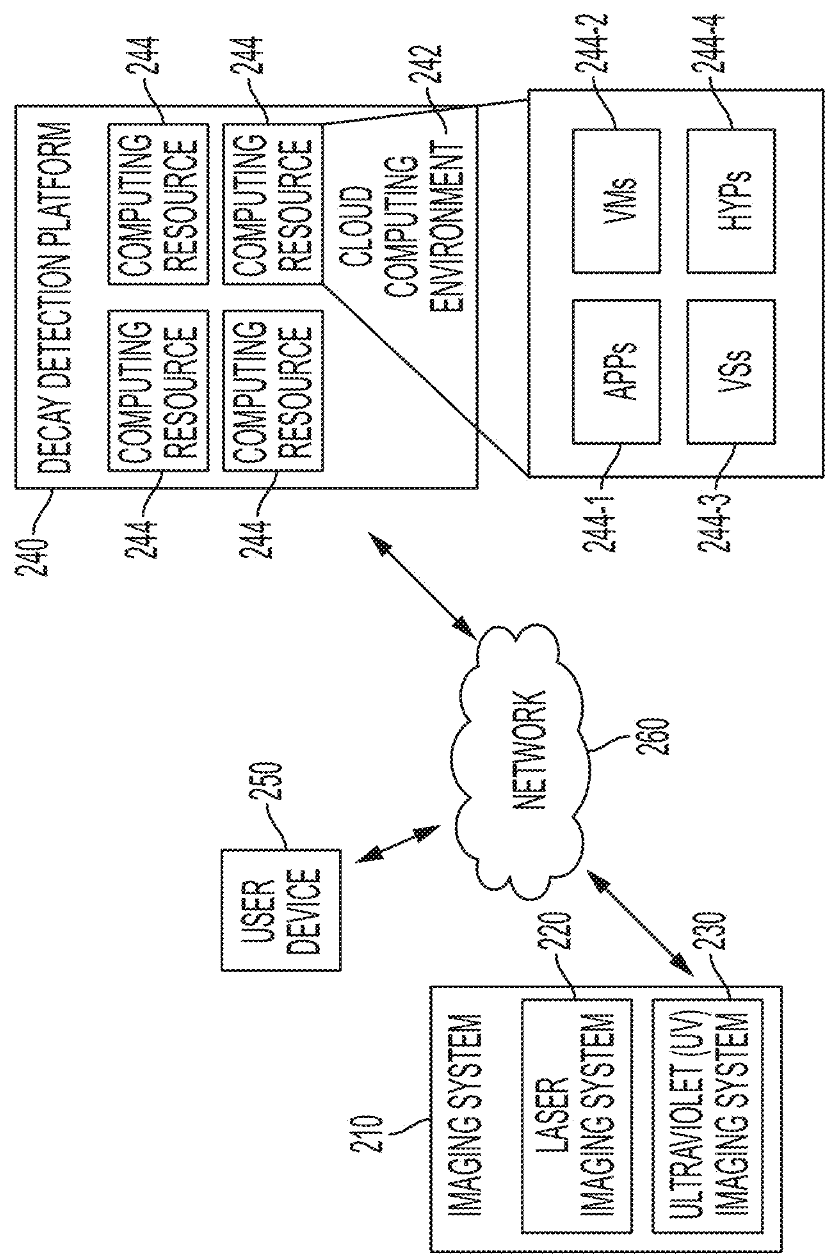
FIG. 2 is a diagram of an example environment according to an embodiment.

FIG. 2 is a diagram of an example environment 200 in which systems and/or methods, described herein, may be implemented. As shown in FIG. 2, environment 200 may include an imaging system 210, a laser imaging system 220, an ultraviolet (UV) imaging system 230, a decay detection platform 240, a user device 250, and a network 260. Devices of environment 200 may interconnect via wired connections, wireless connections, or a combination of wired and wireless connections.

Imaging system 210 includes one or more devices configured to perform imaging of a food product. The imaging system 210 includes the laser imaging system 220 and/or the UV imaging system 230. The imaging system 210 may be disposed in a processing facility that processes food products. For example, the imaging system 210 may be disposed adjacent to (e.g., above, under, to the side of, etc.) a conveyor in a processing facility, and may perform imaging of food products that travel along the conveyor.

The food product may a citrus fruit, such as a lemon, a lime, an orange, a grapefruit, etc. Alternatively, the food product may be a vegetable, meat, poultry, etc. It should be understood that the implementations herein are applicable to myriad types of food products.

Laser imaging system 220 includes one or more devices configured to perform laser imaging of a food product. For example, the laser imaging system 220 may emit laser light towards the food product, and capture images of the food product that is illuminated by the laser light.

UV imaging system 230 includes one or more devices configured to perform UV imaging of a food product. For example, the UV imaging system may emit UV light towards the food product, and capture images of the food product that is illuminated by the UV light.

Decay detection platform 240 includes one or more devices capable of determining a decay value of a food product. The decay detection platform 240 may include a cloud server or a group of cloud servers. The decay detection platform 240 may be designed to be modular such that certain software components may be swapped in or out depending on a particular need. As such, the decay detection platform 240 may be easily and/or quickly reconfigured for different uses.

The decay detection platform 240 may be hosted in cloud computing environment 242. Although embodiments described herein describe decay detection platform 240 as being hosted in cloud computing environment 242, the decay detection platform 240 might not be cloud-based (i.e., may be implemented outside of a cloud computing environment) or may be partially cloud-based.

Cloud computing environment 242 includes an environment that hosts decay detection platform 240. Cloud computing environment 242 may provide computation, software, data access, storage, etc. services that do not require end-user (e.g., user device 250) knowledge of a physical location and configuration of system(s) and/or device(s) that hosts decay detection platform 240. As shown, cloud computing environment 242 may include a group of computing resources 244 (referred to collectively as "computing resources 244" and individually as "computing resource 244").

Computing resource 244 includes one or more personal computers, workstation computers, server devices, or other types of computation and/or communication devices. The computing resource 244 may host decay detection platform 240. The cloud resources may include compute instances executing in computing resource 244, storage devices provided in computing resource 244, data transfer devices provided by computing resource 244, etc. The computing resource 244 may communicate with other computing resources 244 via wired connections, wireless connections, or a combination of wired and wireless connections.

The computing resource 244 includes a group of cloud resources, such as one or more applications ("APPs") 244-1, one or more virtual machines ("VMs") 244-2, virtualized storage ("VSs") 244-3, one or more hypervisors ("HYPs") 244-4, or the like.

Application 244-1 includes one or more software applications that may be provided to or accessed by the user device 250. Application 244-1 may eliminate a need to install and execute the software applications on the user device 250. For example, application 244-1 may include software associated with the decay detection platform 240 and/or any other software capable of being provided via the cloud computing environment 242. One application 244-1 may send/receive information to/from one or more other applications 244-1, via virtual machine 244-2.

Virtual machine 244-2 includes a software implementation of a machine (e.g., a computer) that executes programs like a physical machine. Virtual machine 244-2 may be either a system virtual machine or a process virtual machine, depending upon use and degree of correspondence to any real machine by virtual machine 244-2. A system virtual machine may provide a complete system platform that supports execution of a complete operating system ("OS"). A process virtual machine may execute a single program, and may support a single process. The virtual machine 244-2 may execute on behalf of a user (e.g., user device 250), and may manage infrastructure of cloud computing environment 242, such as data management, synchronization, or long-duration data transfers.

Virtualized storage 244-3 includes one or more storage systems and/or one or more devices that use virtualization techniques within the storage systems or devices of the computing resource 244. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 244-4 may provide hardware virtualization techniques that allow multiple operating systems (e.g., "guest operating systems") to execute concurrently on a host computer, such as the computing resource 244. The hypervisor 244-4 may present a virtual operating platform to the guest operating systems, and may manage the execution of the guest operating systems. Multiple instances of a variety of operating systems may share virtualized hardware resources.

User device 250 includes one or more devices capable of receiving, generating, storing, processing, and/or providing information associated with the decay detection platform 240. For example, the user device 250 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. The user device 250 may receive information from and/or transmit information to the decay detection platform 240, the imaging system 210, the laser imaging system 220, the UV imaging system 220, and other user devices 250.

Network 260 includes one or more wired and/or wireless networks. For example, network 260 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. A set of devices (e.g., one or more devices) of environment 200 may perform one or more functions described as being performed by another set of devices of environment 200.

Figure 3:
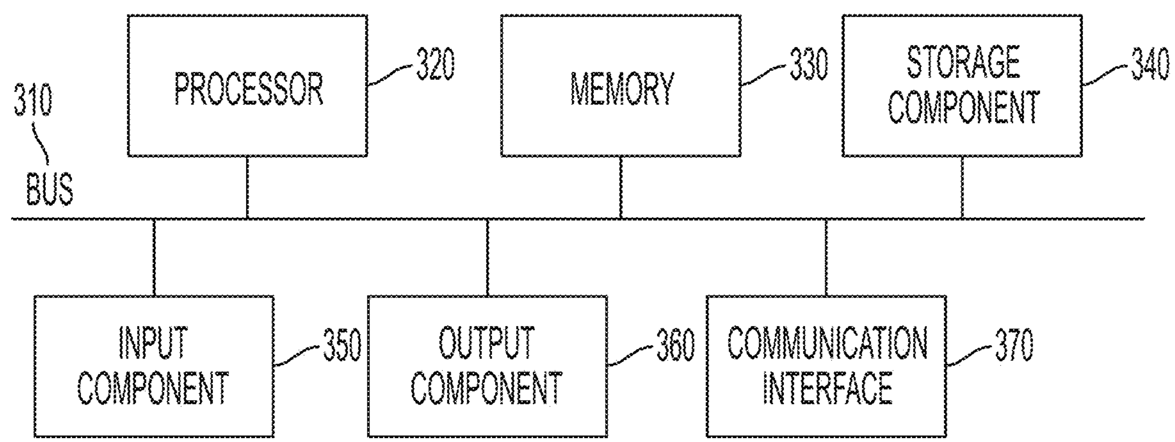
FIG. 3 is a diagram of example components of one or more devices of FIG. 2 according to an embodiment.

FIG. 3 is a diagram of example components of a device 300. Device 300 may correspond to the imaging system 210, the laser imaging system 220, the UV imaging system 230, the decay detection platform 240, and/or the user device 250. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. The processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). The input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Hardwired circuitry may be used in place of or in combination with software instructions to perform one or more processes described herein. Embodiments herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
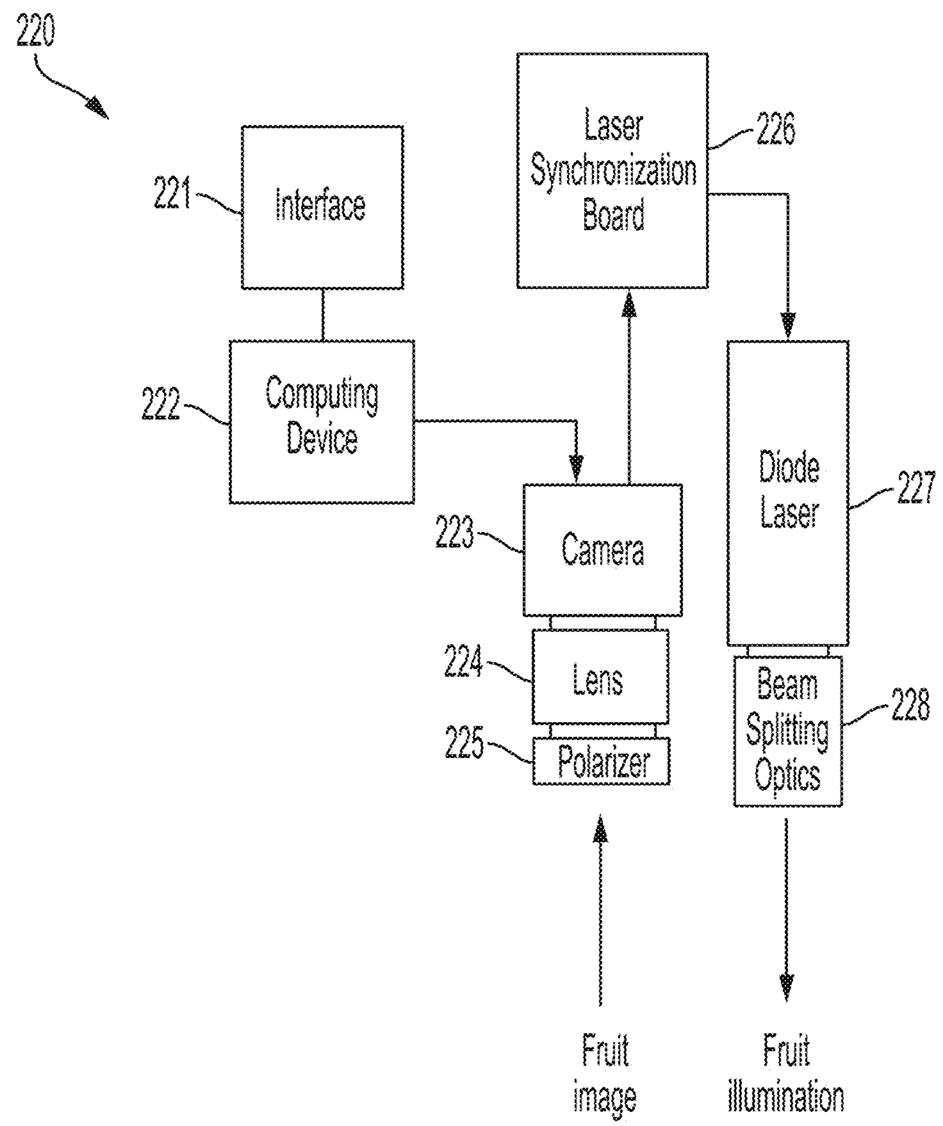
FIG. 4 is a diagram of a laser imaging system according to an embodiment.

FIG. 4 is a diagram of a laser imaging system 220 according to an embodiment. As shown in FIG. 4, the laser imaging system 220 may include an interface 221, a computing device 222, a camera 223, a lens 224, a polarizer 225, a laser synchronization board 226, a diode laser 227, and beam splitting optics 228.

The interface 221 includes an interface that is configured to connect to the decay detection platform 240 and/or the user device 250. The interface 221 is configured to permit the laser imaging system 220 to communicate with the decay detection platform 240 and/or the user device 250. The computing device 222 is configured to control the components of the laser imaging system 220. For example, the computing device 222 includes a processor, a controller, a memory, etc.

The camera 223 and lens 224 are configured to capture an image of a food product. For example, the camera 223 may receive a trigger signal from the computing device 222, and capture the image of the food product based on the trigger signal. The computing device 222 may monitor conveyor movement, and send the trigger signal based on the food product being positioned in a predetermined capturing range of the camera 223. The polarizer 225 is disposed on the lens 224, and is configured to block laser specular reflection (glare), and transmit the diffuse backscatter.

As a particular example, the camera 223 may be configured with a fan angle of 27.6 degrees, and include a capturing region having a width of 13.5 inches. Further, the camera 223 may be disposed 27.5 inches above the food product.

The laser synchronization board 226 is configured to receive a camera signal from the camera 223, and control the diode laser 227 to emit light simultaneously with operation of the camera 223, to permit the camera 223 to capture the laser image of the food product.

The diode laser 227 is configured to emit laser light towards the food product. The beam splitting optics 228 is configured to split the laser light into a pattern of lines. For example, the beam splitting optics 228 is configured to split the laser light into a predetermined pattern. For example, the beam splitting optics 228 is configured to split the laser light into a set of parallel lines.

As a particular example, the beam splitting optics 228 is configured to split the laser light into a set of 21 lines each having a width of 0.25 inches. Further, the beam splitting optics 228 is configured to cause the laser light to have a fan angle of 10.4 degrees, with an inter-beam angle of 0.5 degrees per line. Further still, the beam splitting optics 228 is configured to cause the laser light to illuminate an illumination region having a width of 5 inches.

Figure 5:
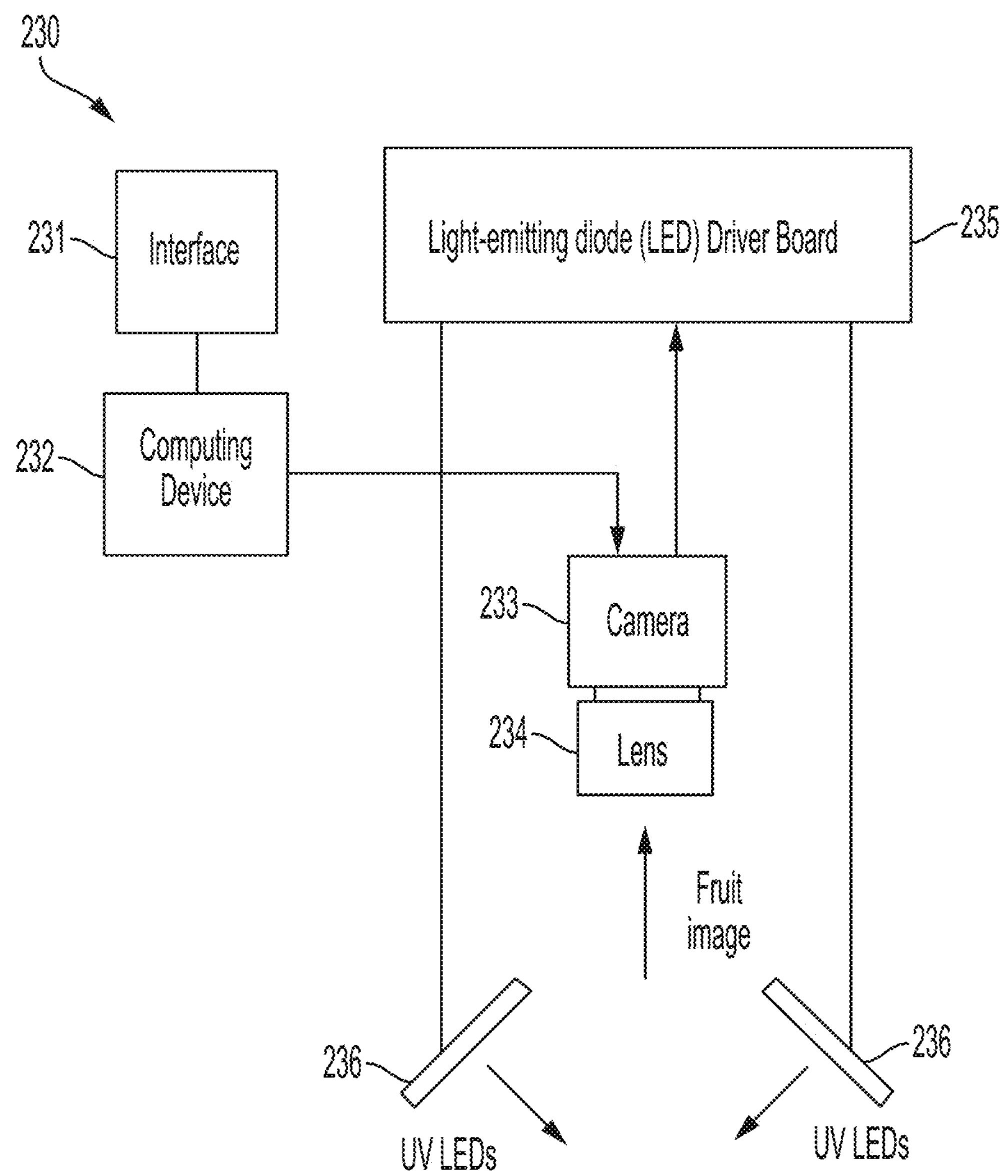
FIG. 5 is a diagram of an ultraviolet (UV) imaging system according to an embodiment.

FIG. 5 is a diagram of an ultraviolet (UV) imaging system according to an embodiment. As shown in FIG. 5, the UV imaging system 230 may include an interface 231, a computing device 232, a camera 233, a lens 234, a light-emitting diode (LED) driver board 235, and UV LEDs 236.

The interface 231 includes an interface that is configured to connect to the decay detection platform 240 and/or the user device 250. The interface 231 is configured to permit the UV imaging system 230 to communicate with the decay detection platform 240 and/or the user device 250. The computing device 232 is configured to control the components of the UV imaging system 230. For example, the computing device 222 includes a processor, a controller, a memory, etc.

The camera 233 and lens 234 are configured to capture an image of a food product. For example, the camera 233 may receive a trigger signal from the computing device 232, and capture the image of the food product based on the trigger signal. The computing device 232 may monitor conveyor movement, and send the trigger signal based on the food product being positioned in a predetermined capturing range of the camera 233.

The light-emitting diode (LED) driver board 235 is configured to receive a camera signal from the camera 233, and control the UV LEDs 236 to emit light simultaneously with operation of the camera 233, to permit the camera 233 to capture the laser image of the food product.

The UV LEDs 236 are configured to emit UV light towards the food product. For example, the UV LEDs 236 may emit UV light having a wavelength range of 315 to 400 nanometers (nms), with a peak of 365 nm towards the food product.

Figure 6:
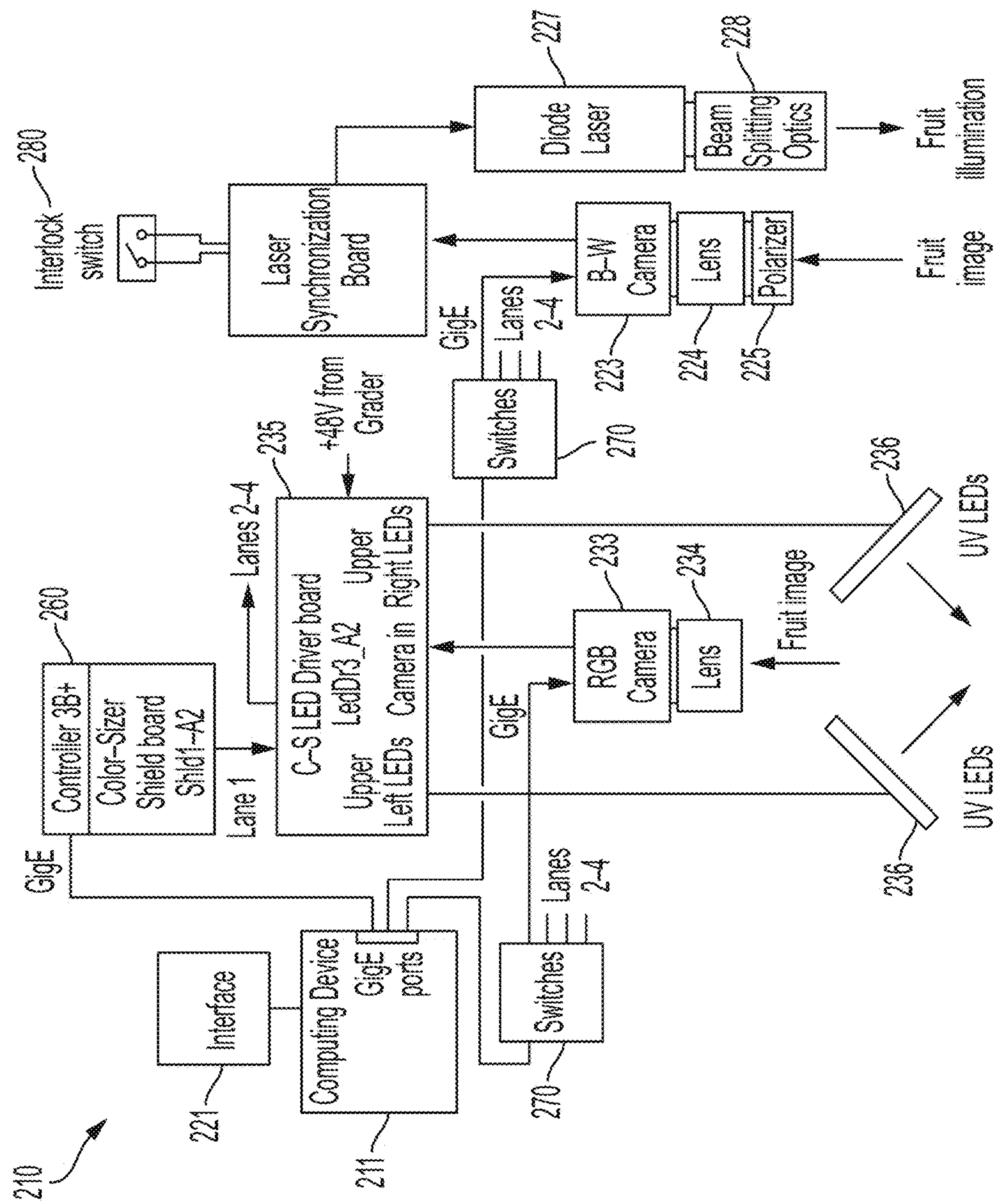
FIG. 6 is a diagram of an imaging system according to an embodiment.

FIG. 6 is a diagram of an imaging system according to an embodiment. As shown in FIG. 6, the imaging system 210 may include one or more of the components of the laser imaging system 220 and/or the UV imaging system 230. Further, as shown in FIG. 6, the imaging system 210 may include a controller 260, switches 270, and an interlock switch 280. The controller 260 and the switches 270 may be configured to permit the computing device 211 to control the laser imaging system 220 and the UV imaging system 230, and permit the imaging system 210 to operate concurrently with other imaging systems 210 (e.g., associated with other conveyor systems or lanes). The interlock switch 280 may be configured to prevent the laser imaging system 220 from operating in certain conditions.

The imaging system 210 may include a grader camera that detects a position of the food product on the conveyor system. Based on the position of the food product, the imaging system 210 may control the laser imaging system 220 and the UV imaging system 230 to capture laser images and UV images, respectively, of the food product. The laser imaging system 220 and the UV imaging system 230 may be configured to capture respective images in a predetermined timing pattern.

Figure 7:
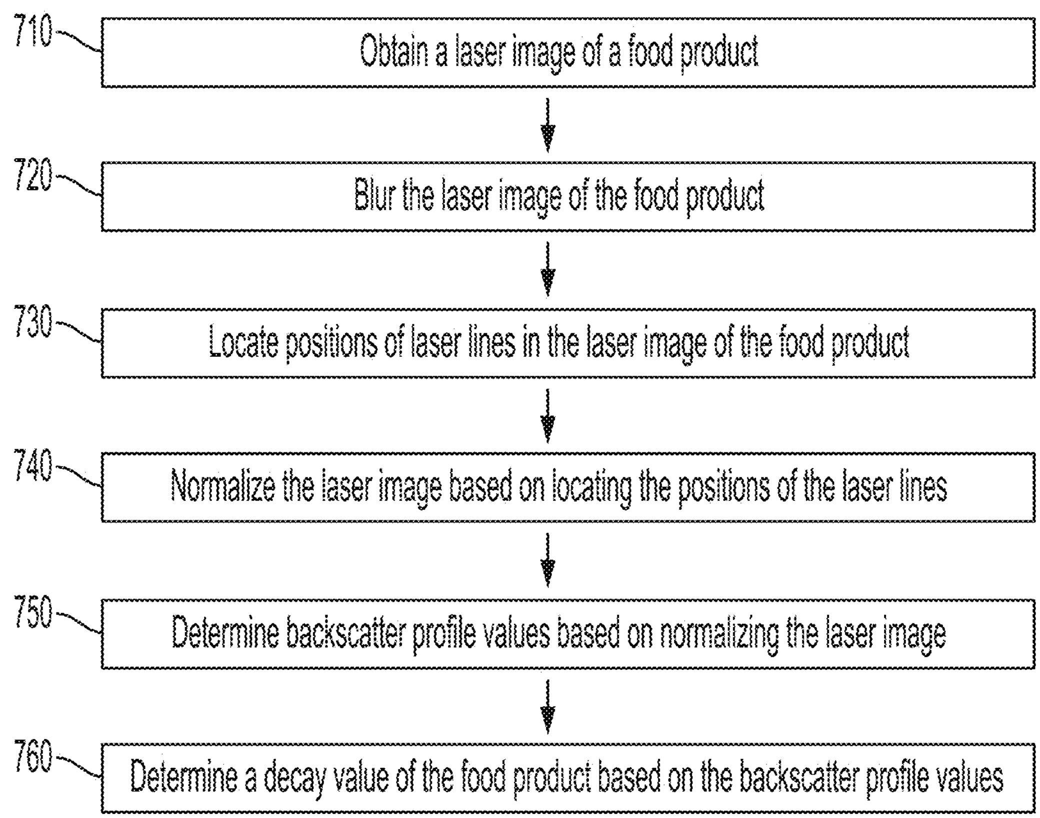
FIG. 7 is a flow chart of a process for determining a decay value of a food product based on laser imaging according to an embodiment.

FIG. 7 is a flow chart of a process for determining a decay value of a food product based on laser imaging according to an embodiment. One or more operations of FIG. 7 may be performed by decay detection platform 240. Additionally, or alternatively, one or more operations of FIG. 7 may be performed by another device or a group of devices separate from or including decay detection platform 240, such as imaging system 210, laser imaging system 220, UV imaging system 230, and/or user device 250.

As shown in FIG. 7, process 700 may include obtaining a laser image of a food product (operation 710). For example, the decay detection platform 240 may obtain a laser image of a food product from the laser imaging system 220. The laser imaging system 220 may obtain a predetermined number of laser images of the food product, and provide the predetermined number of laser images to the decay detection platform 240. The predetermined number of laser images may be five laser images, ten laser images, thirty laser images, etc. The laser images may be monochrome laser images, color laser images, etc.

Figure 8A:
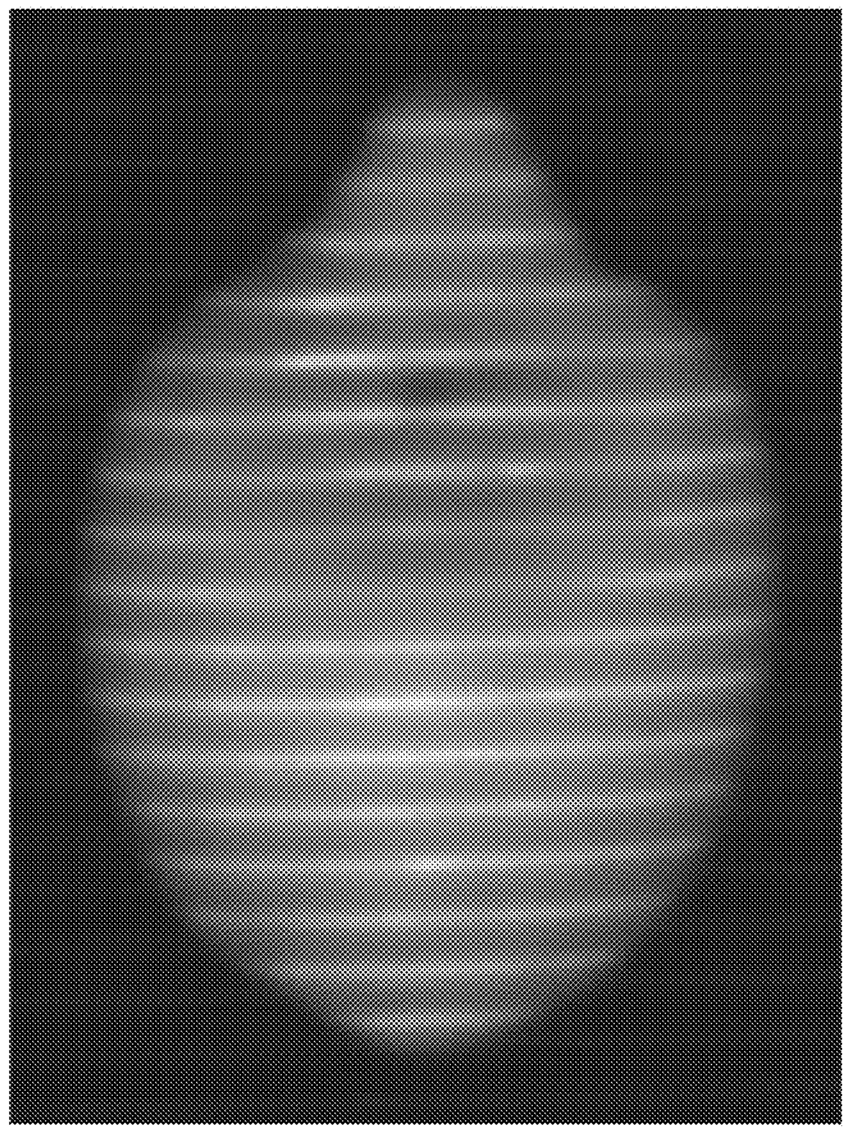
FIGS. 8A-8E are diagrams of laser images according to an embodiment.

As further shown in FIG. 7, process 700 may include blurring the laser image (operation 720). For example, and referring to FIG. 8A, the decay detection platform 240 may blur the laser image to reduce laser speckle and variation. The decay detection platform 240 may blur the laser image in a horizontal direction. For example, the decay detection platform 240 may blur the laser image in the horizontal direction by averaging over a predetermined number of pixels, over a predetermined distance, etc.

Figure 8B:
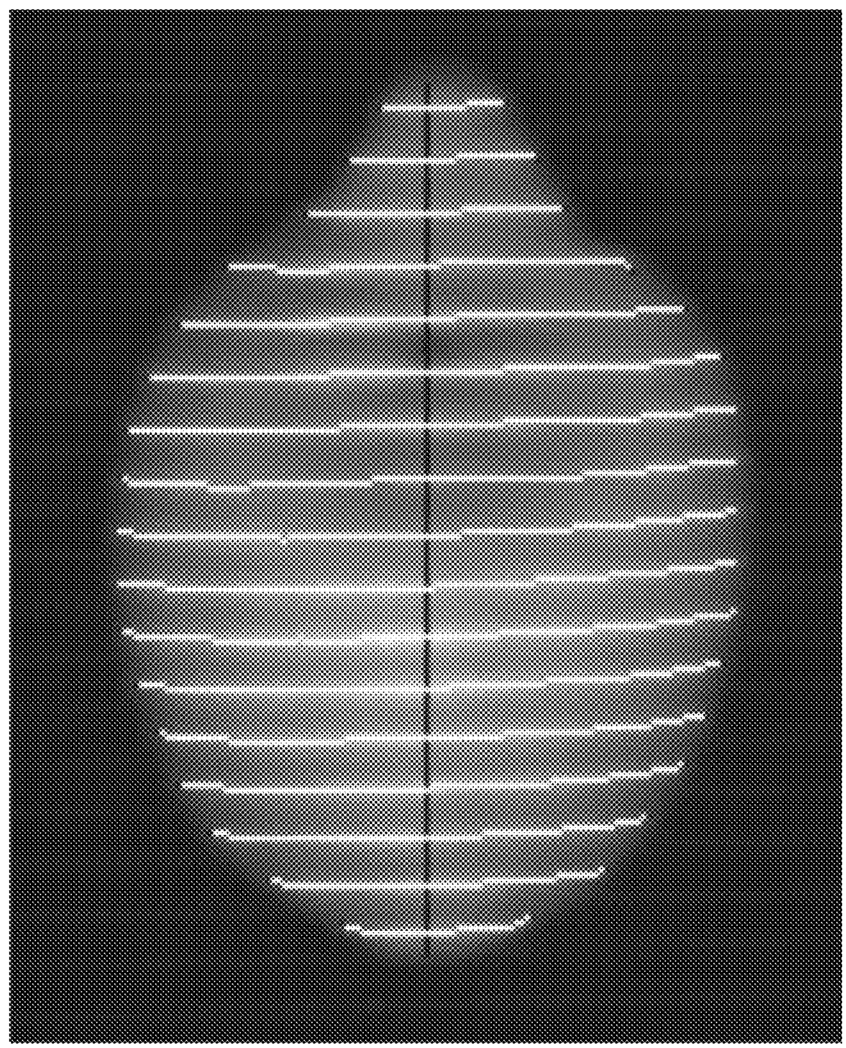

As further shown in FIG. 7, process 700 may include locating positions of laser lines in the laser image of the food product (operation 730). For example, and referring to FIG. 8B, the decay detection platform 240 may locate positions of laser lines in the laser image of the food product by identifying a center column of the laser image, and doing a convolution between a kernel and the laser image. As an example, the kernel may be a 3×3 kernel of [−1, −1, −1; 2, 2, 2; −1, −1, −1]. Further, the decay detection platform 240 may threshold the results of the convolution to locate the positions of the laser lines. Further still, the decay detection platform 240 may remove particular vertical points by selecting a largest gray value near the average line spacing. Further still, the decay detection platform 240 may fill in any missing points by using the brightest pixel at the average line spacing. Further still, the decay detection platform 240 may search horizontally from the center column to the edge of the food product on the brightest pixels.

Figure 8C:
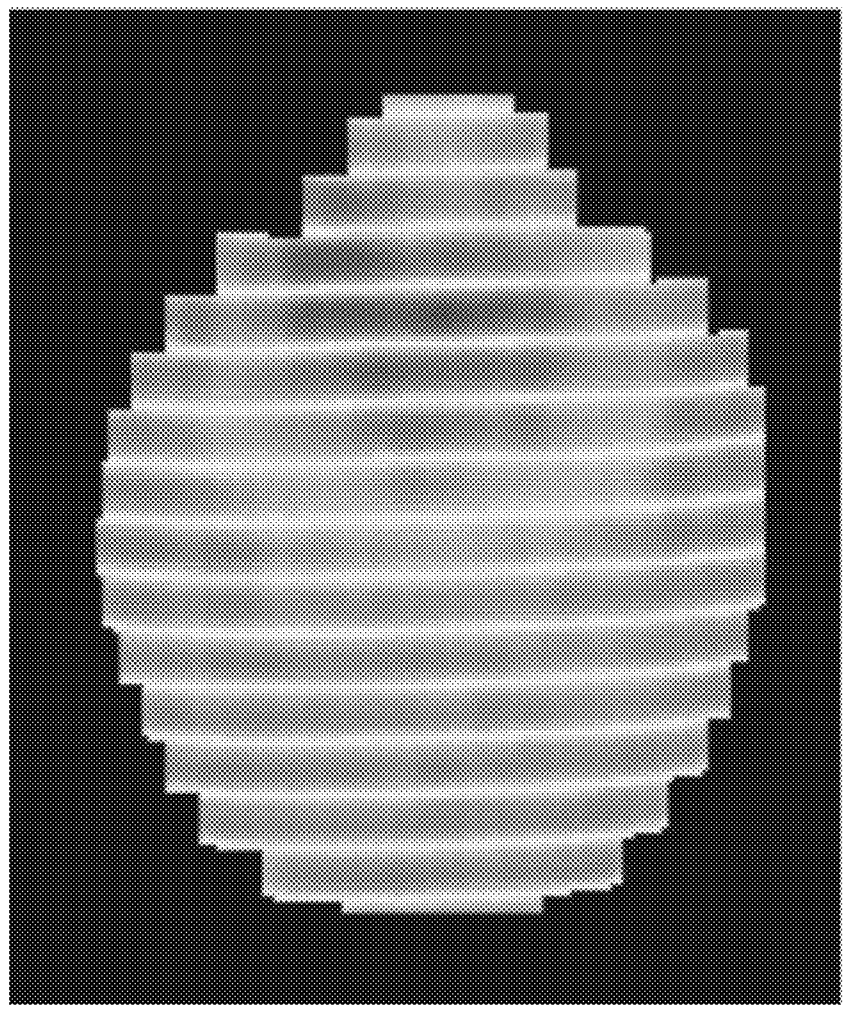

As further shown in FIG. 7, process 700 may include normalizing the laser image based on locating the positions of the laser lines (operation 730). For example, and referring to FIG. 8C, the decay detection platform 240 may normalize the laser image by using line point values to increase the image brightness at the edges of the food product to render the image brightness uniform across the food product. To do so, the decay detection platform 240 may determine a correction factor at each line point to render each line point of the same brightness. Further, the decay detection platform 240 may interpolate vertically between the lines to estimate a correction factor for the pixels between the lines. Further still, the decay detection platform 240 may generate a new image based on the correction factors. In this way, the light and dark decay regions may provide a more consistent response across the surface of the food product.

Figure 8D:
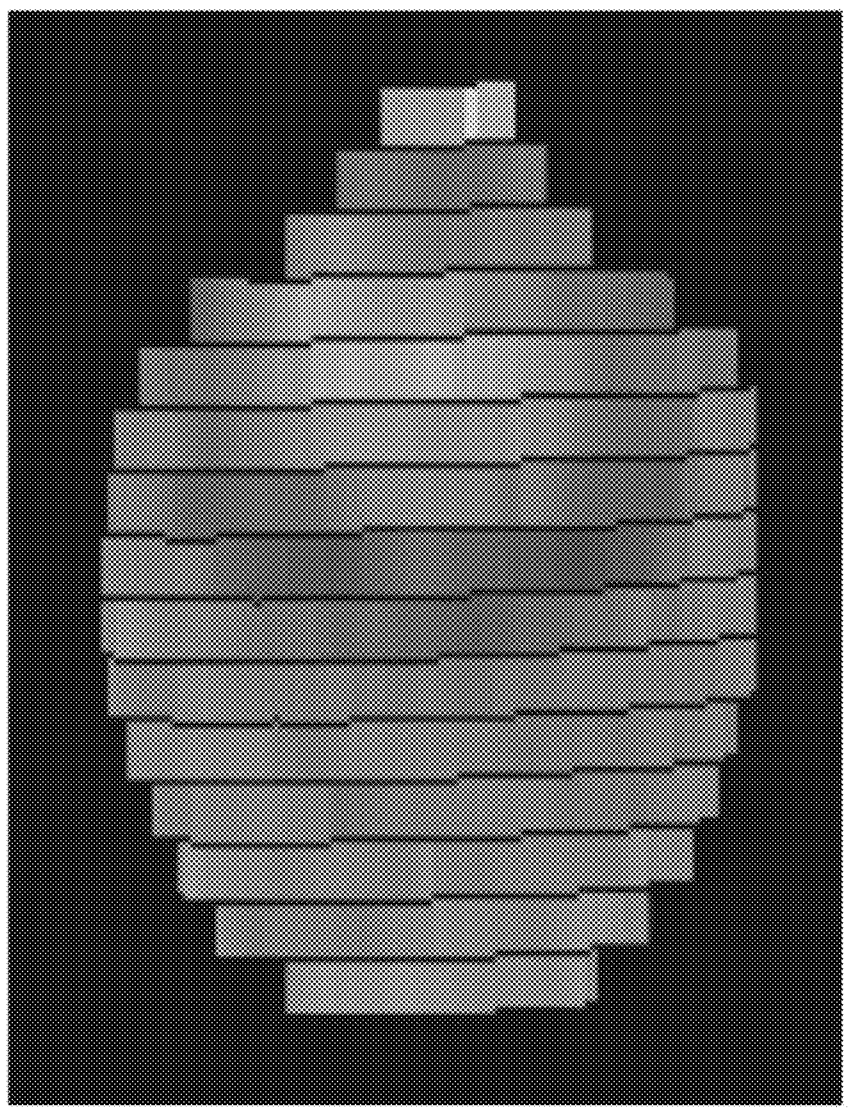

As further shown in FIG. 7, process 700 may include determining backscatter profile values based on normalizing the laser image (operation 740). For example, and referring to FIG. 8D, the decay detection platform 240 may determine the quadratic regression on the intensities of the vertical pixels between two laser lines to measure the shape. Further, the decay detection platform 240 may fit the points to $y=ax^2+bx+c$. Further still, the decay detection platform 240 may use the values for "a" as the profile values.

In this way, the decay detection system 240 determines a profile value that is related to the shape of the pixel intensities of the vertical line between two laser points. The intensities may form a somewhat parabolic curve that indicates how the light is diffusing through the skin of the food product. Clear rot provides a shallow curve due to the increased scatter of light in the damaged skin. Advanced decay provides a deep curve due to most of the light passing though into the interior of the food product. The image shows the profile values as intensities. Clear rot regions appear dark and advanced decay regions are the lightest.

Figure 8E:
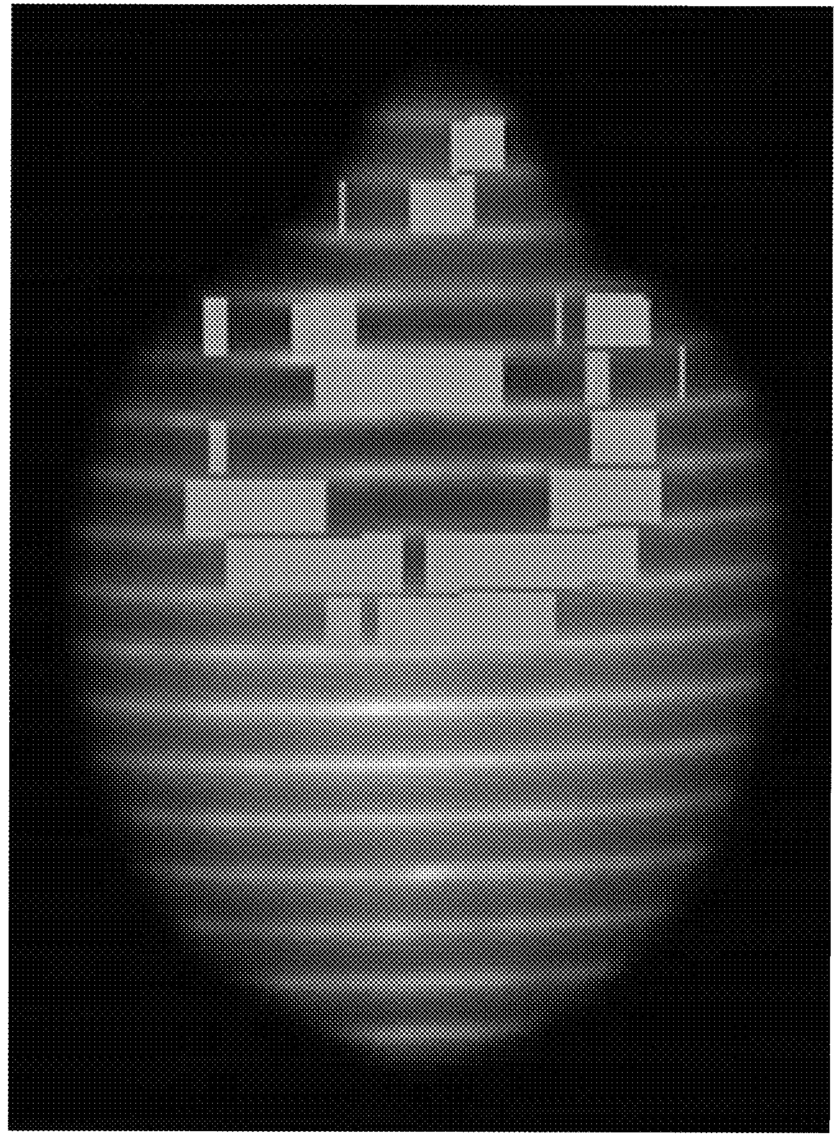

As further shown in FIG. 7, process 700 may include determining a decay value of the food product based on the backscatter profile values (operation 750). For example, and referring to FIG. 8E which depicts marked regions where the backscatter profile values are outside of the thresholds, the decay detection platform 240 may compare the backscatter profile values to a set of thresholds, and determine the decay values based on the comparison.

The set of thresholds may include a low threshold, and a high threshold. Further, the set of thresholds may be predetermined based on the type of food product, the size of the food product, etc. Backscatter profile values that are greater than the high threshold may be indicative of decay (e.g., late decay), and the backscatter profile values that are less than the low threshold may be indicative of decay (e.g., early decay). The decay detection platform 240 may determine a decay value based on the number of backscatter profile values that are greater than or less than the set of thresholds. For example, the decay detection platform 240 may sum the backscatter profile values of all of the detected pixels that are greater than or less than the set of thresholds.

The decay detection platform 240 may determine a decay value for each of a set of laser images of the food product. Further, the decay detection platform 240 may determine a total decay value for the food product based on the set of decay values corresponding to the set of laser images.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Figure 9:
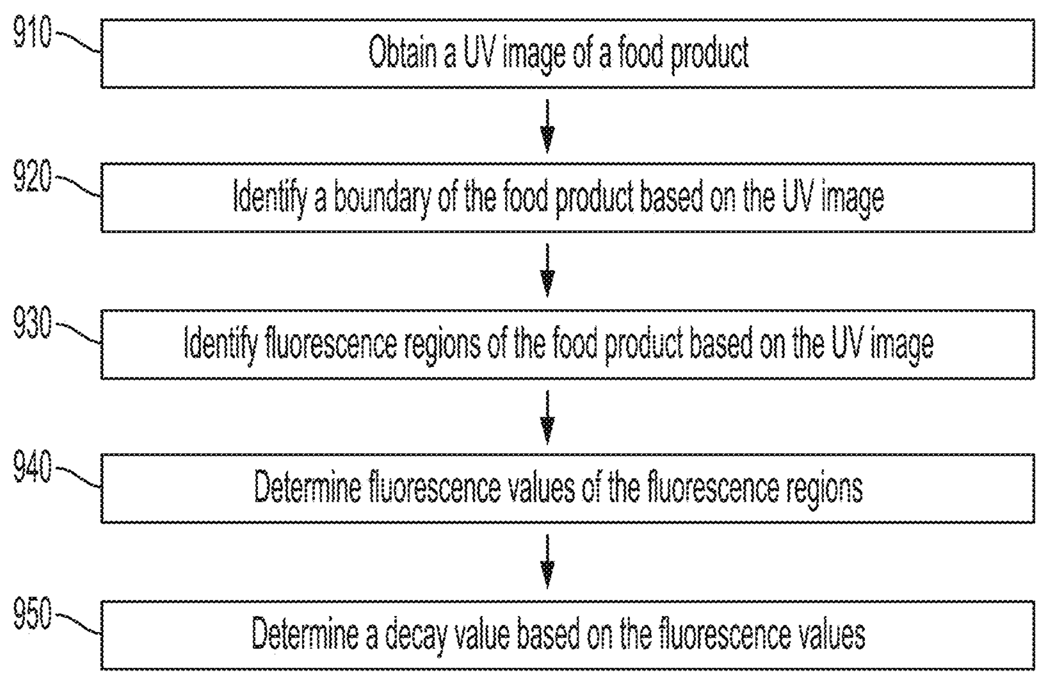
FIG. 9 is a flow chart of an example process for determining a decay value based on UV imaging according to an embodiment.

FIG. 9 is a flow chart of an example process for determining a decay value of a food product based on UV imaging according to an embodiment.

One or more operations of FIG. 9 may be performed by decay detection platform 240. Additionally, or alternatively, one or more operations of FIG. 9 may be performed by another device or a group of devices separate from or including decay detection platform 240, such as imaging system 210, laser imaging system 220, UV imaging system 230, and/or user device 250.

As shown in FIG. 9, process 900 may include obtaining a UV image of a food product (operation 910). For example, the decay detection platform 240 may obtain a UV image of a food product from the UV imaging system 230. The UV imaging system 230 may obtain a predetermined number of UV images of the food product, and provide the predetermined number of UV images to the decay detection platform 240. The predetermined number of UV images may be five UV images, ten UV images, thirty laser UV, etc.

Figure 10:
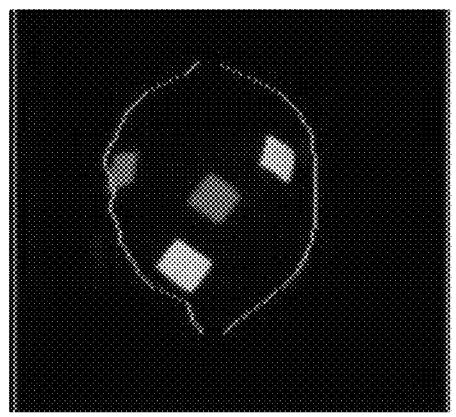
FIG. 10 is a diagram of a UV image according to an embodiment.

As further shown in FIG. 9, process 900 may include identifying a boundary of the food product (block 920). For example, and as shown in FIG. 10, the decay detection platform 240 may identify the boundary of the food product based on the laser images. In this case, the decay detection platform 240 may align the boundary of the food product in a laser image with a boundary of the food product in the UV image using x and y offset settings.

As further shown in FIG. 9, process 900 may include identifying fluorescence regions of the food product based on the UV image (operation 930). For example, and as shown in FIG. 10, the decay detection platform 240 may identify a region of the food product that includes a luminance value that is greater than a luminance threshold.

As further shown in FIG. 9, process 900 may include determining fluorescence values of the fluorescence regions (operation 930). For example, the decay detection platform 240 may determine red, green, and blue (RGB) values of the pixels.

As further shown in FIG. 9, process 900 may include determining a decay value based on the fluorescence values (operation 940). For example, the decay detection platform 240 may determine a decay value based on the RGB values. The decay detection platform 240 may use a map that maps an RGB value to a decay value. Further, the decay detection platform 240 may determine a decay value for each pixel based on the RGB values, and then determine a decay value for the food product based on the decay values for each of the pixels. The map may correspond to the type of food product. For example, a first type of food product may be associated with a first map, and a second type of food product may be associated with a second type of map.

The decay detection platform 240 may determine a decay value for each of a predetermined number of UV images of the food product, and determine a total decay value based on the respective decay values.

Although FIG. 9 shows example blocks of process 900, in some implementations, process 900 may include additional blocks, fewer blocks, different blocks, or differently arranged blocks than those depicted in FIG. 9. Additionally, or alternatively, two or more of the blocks of process 900 may be performed in parallel.

Figure 11:
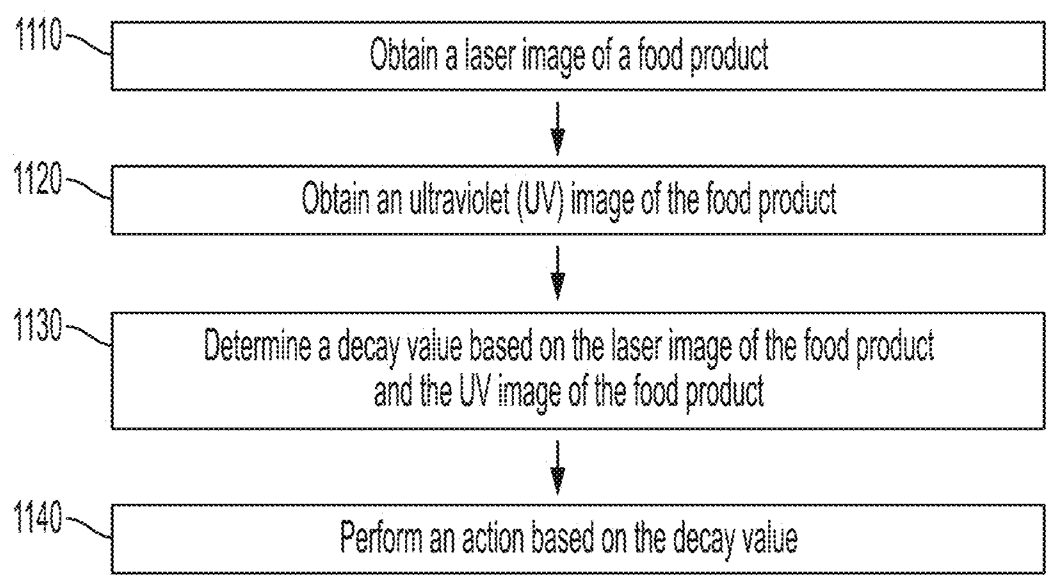
FIG. 11 is a flow chart of a process for determining a decay value of a food product based on laser imaging and UV imaging according to an embodiment.

FIG. 11 is a flow chart of a process for determining a decay value of a food product based on laser imaging and UV imaging according to an embodiment.

One or more operations of FIG. 11 may be performed by decay detection platform 240. Additionally, or alternatively, one or more operations of FIG. 11 may be performed by another device or a group of devices separate from or including decay detection platform 240, such as imaging system 210, laser imaging system 220, UV imaging system 230, and/or user device 250.

As shown in FIG. 11, process 1100 may include obtaining a UV image of a food product (operation 1110). For example, the decay detection platform 240 may obtain a laser image of the food product in a similar manner as described above in association with FIG. 7.

As further shown in FIG. 11, process 1100 may include obtaining an ultraviolet (UV) image of the food product (operation 1120). For example, the decay detection platform 240 may obtain a UV image of the food product in a similar manner as described above in association with FIG. 9.

As further shown in FIG. 11, process 1100 may include determining a decay value based on obtaining the laser image of the food product and the UV image of the food product (operation 1130). For example, the decay detection platform 240 may determine one or more decay values for the food product in a similar manner as described above regarding FIGS. 7 and 9.

The decay detection platform 240 may determine, using the laser image, an early decay value that is indicative of early decay of the food product. Additionally, or alternatively, the decay detection platform 240 may determine, using the laser image, a late decay value that is indicative of late decay of the food product. Additionally, or alternatively, the decay detection platform 240 may determine, using the UV image, a UV decay value that is indicative of UV fluorescence decay.

The decay detection platform 240 may determine a total decay value that is based on one or more of the early decay value, the late decay value, and the UV value. Further, the decay detection platform 240 may assign weights to the foregoing decay values, and determine the total decay value based on the assigned weights. Further still, the decay detection platform 240 may perform a mathematical operation using the foregoing decay values, and determine the total decay value based on performing the mathematical operation.

As further shown in FIG. 11, process 1100 may include performing an action based on the decay value (operation 1140). For example, the decay detection platform 240 may perform an action based on the decay value, such as by causing the food product to be removed from the conveyor, causing the food product to be flagged for further inspection, sending a message to another device, providing image information to the user device 250, and/or the like.

Although FIG. 11 shows example blocks of process 1100, in some implementations, process 1100 may include additional blocks, fewer blocks, different blocks, or differently arranged blocks than those depicted in FIG. 11. Additionally, or alternatively, two or more of the blocks of process 1100 may be performed in parallel.

Figure 12:
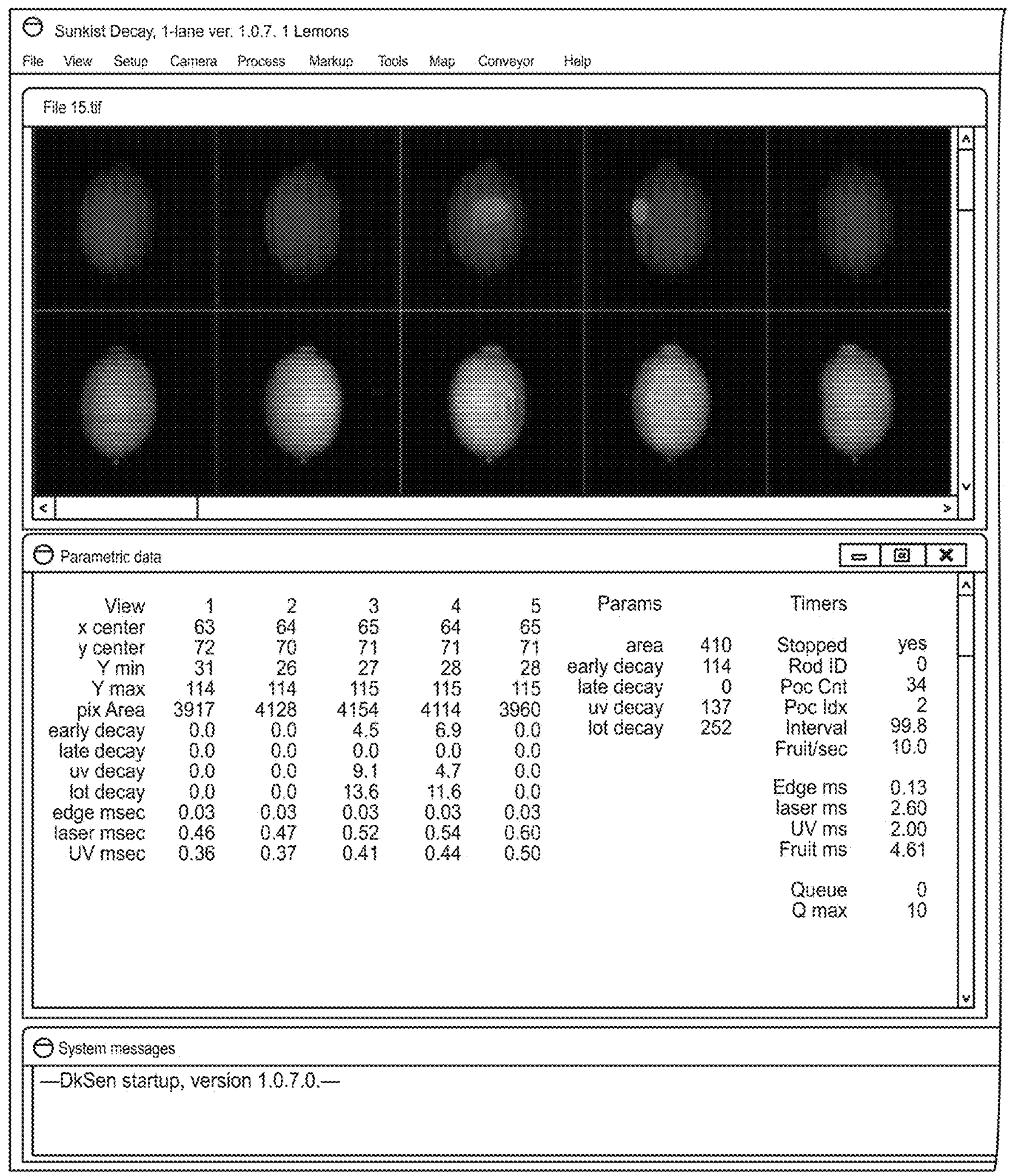
FIG. 12 is a diagram of an example user interface (UI) for displaying a decay value of a food product according to an embodiment.
Figure 12:
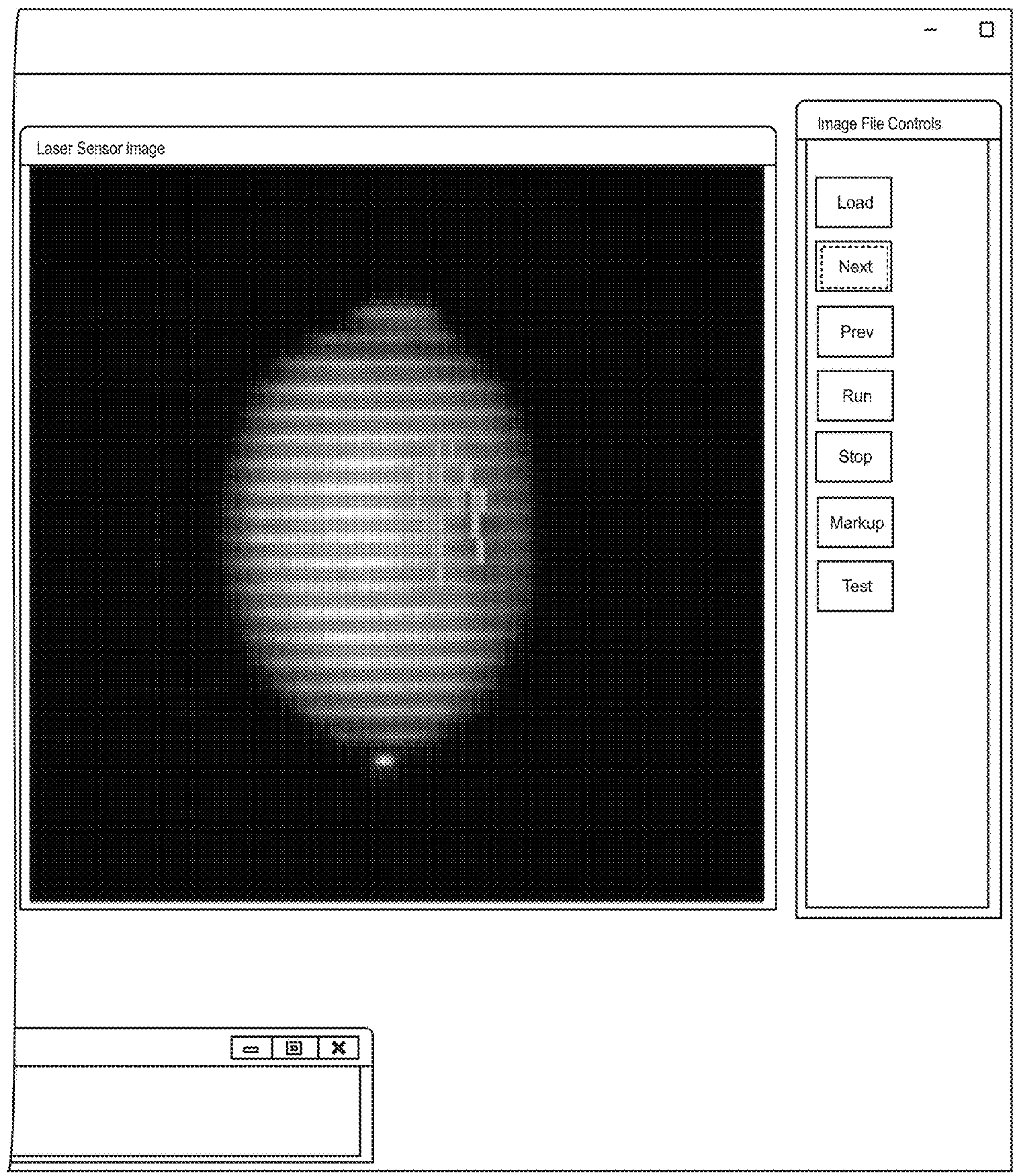

FIG. 12 is a diagram of an example user interface (UI) for displaying a decay value of a food product according to an embodiment.

The decay detection platform 240 may provide image information and food product parameter information to the user device 250. The user device 250 may provide, for display via a UI, the image information and the food product parameter information. For example, the user device 250 may display the laser images and/or the UV images that are annotated to indicate decay regions. Further, the user device 250 may display food product parameter information, such as decay values. In this way, an operator of the user device 250 may view the information to analyze the food product.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
- obtaining a laser image of a food product, wherein the laser image comprises at least two laser lines;
- determining a profile value of light within a region between said two laser lines;
- determining a decay value of the food product based on said profile value; and
- blurring the laser image in a horizontal direction of the laser image;
- generating the decay value based on blurring the laser image in the horizontal direction of the laser image.

2. The method of claim 1, further comprising:
- performing an action associated with the food product based on the decay value.

3. The method of claim 1, further comprising:
- obtaining an ultraviolet image (UV) of the food product; and
- determining the decay value based on the profile value and the ultraviolet image.

4. The method of claim 3, further comprising:
- determining red, green, and blue (RGB) values of pixels of the UV image; and
- determining the decay value based on the RGB values of the pixels of the UV images.

5. The method of claim 1, further comprising:
- locating positions of laser lines in the laser image;
- determining backscatter profile values based on the positions of the laser lines; and
- determining the decay value based on the backscatter profile values.

6. The method of claim 1, wherein the food product is a citrus fruit.

7. A device, comprising:
- a memory configured to store instructions; and
- a processor configured to execute the instructions to:
- obtain a laser image of a food product, wherein the laser image comprises at least two laser lines;
- determine a profile value of light within a region between said two laser lines; and
- determine a decay value of the food product based on said profile value,
- blur the laser image in a horizontal direction of the laser image; and
- generate the decay value based on blurring the laser image in the horizontal direction of the laser image.

8. The device of claim 7, wherein the processor is further configured to:
- perform an action associated with the food product based on the decay value.

9. The device of claim 7, wherein the processor is further configured to:

obtain an ultraviolet image (UV) of the food product; and determine the decay value based on the profile value and the ultraviolet image.

10. The device of claim 9, wherein the processor is further configured to:

locating positions of laser lines in the laser image;

determine backscatter profile values based on the positions of the laser lines; and determine the decay value based on the backscatter profile values.

11. The device of claim 7, wherein the processor is further configured to:

determine red, green, and blue (RGB) values of pixels of the UV image; and determine the decay value based on the RGB values of the pixels of the UV images.

12. The device of claim 7, wherein the food product is a citrus fruit.

13. A non-transitory computer-readable medium storing instructions, the instructions comprising: one or more instructions that, when executed by one or more processors of a device, cause the one or more processors to:

obtain a laser image of a food product, wherein the laser image comprises at least two laser lines;

determine a profile value of light within a region between said two laser lines;

determine a decay value of the food product based on said profile value;

blur the laser image in a horizontal direction of the laser image; and generate the decay value based on blurring the laser image in the horizontal direction of the laser image.

14. The non-transitory computer-readable medium of claim 13, wherein the one or more instructions further cause the one or more processors to:

perform an action associated with the food product based on the decay value.

15. The non-transitory computer-readable medium of claim 13, wherein the one or more instructions further cause the one or more processors to:

obtain an ultraviolet image (UV) of the food product; and determine the decay value based on the profile value of the ultraviolet image.

16. The non-transitory computer-readable medium of claim 13, wherein the one or more instructions further cause the one or more processors to:

determine red, green, and blue (RGB) values of pixels of the UV image; and determine the decay value based on the RGB values of the pixels of the UV images.

17. The non-transitory computer-readable medium of claim 13, wherein the food product is a citrus fruit.

18. A method for detecting decay of a food product, the method comprising the steps of:

a) obtaining a laser image of a food product, wherein the laser image comprises a plurality of laser lines;

b) locating the position of at least two of said plurality of laser lines;

c) determining a profile value based on the intensity of pixels between the at least two laser lines located in the step b); and d) determining a decay value of said food product based on the profile value determined in step c); and e) blurring the laser image in a horizontal direction of the laser image;

f) generating the decay value based on blurring the laser image in the horizontal direction of the laser image.

19. The method according to claim 18, further comprising the step of:

g) obtaining a UV image of said food product, wherein the decay value of said food product determined in step d) is determined based on the profile value determined in step c) and the UV image obtained in step e).

* * * * *